(12) United States Patent
Couture (10) Patent No.: US 8,512,336 B2
(45) Date of Patent: Aug. 20, 2013

(54) OPTIMAL GEOMETRIES FOR CREATING CURRENT DENSITIES IN A BIPOLAR ELECTRODE CONFIGURATION

(75) Inventor: Gary M. Couture, Longmont, CO (US)

(73) Assignee: Covidien LP, Mansfield, MA (US)

( * ) Notice: Subject to any disclaimer, the term of this patent is extended or adjusted under 35 U.S.C. 154(b) by 265 days.

(21) Appl. No.: 12/832,772

(22) Filed: Jul. 8, 2010

(65) Prior Publication Data

US 2012/0010614 A1    Jan. 12, 2012

(51) Int. Cl.
*A61B 18/18* (2006.01)

(52) U.S. Cl.
USPC .................... 606/45; 606/50; 606/51; 606/52

(58) Field of Classification Search
USPC ...................................... 606/50–52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,833,690 A * | 11/1998 | Yates et al. ............ 606/52 |
| D402,028 S | 12/1998 | Grimm et al. |
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Linda Dvorak
*Assistant Examiner* — Amanda Scott (57) ABSTRACT

An end effector assembly for use with an electrosurgical instrument is provided. The end effector assembly has a first jaw member having a first pair of tissue contacting surfaces and an insulator disposed therebetween. The end effector assembly also has a second jaw member that includes a second pair of tissue contacting surfaces, a pair of insulators disposed between the second pair of tissue contacting surfaces, and a cutting element disposed between the pair of insulators. The relative movement of the first jaw member toward the second jaw member causes the insulator of the first jaw member and the pair of insulators of the second jaw member to pinch tissue disposed between the first jaw member and the second jaw member.

13 Claims, 4 Drawing Sheets

(56) References Cited

U.S. PATENT DOCUMENTS

| | | | |
|---|---|---|---|
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,169,146 B2* | 1/2007 | Truckai et al. | 606/41 |
| D538,932 S | 3/2007 | Malik | |
| 7,195,631 B2* | 3/2007 | Dumbauld | 606/51 |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| 7,232,440 B2* | 6/2007 | Dumbauld et al. | 606/51 |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,487,780 B2 | 2/2009 | Hooven | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 2002/0107517 A1* | 8/2002 | Witt et al. | 606/50 |
| 2003/0171748 A1 | 9/2003 | Truckai et al. | |
| 2006/0116675 A1 | 6/2006 | McClurken et al. | |
| 2008/0058802 A1 | 3/2008 | Couture et al. | |
| 2008/0195093 A1 | 8/2008 | Couture et al. | |
| 2011/0178519 A1 | 7/2011 | Couture et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1894535 | 3/2008 |
| EP | 1958583 | 8/2008 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 09/591,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.

U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11173008.1 dated Oct. 21, 2011.

* cited by examiner

OPTIMAL GEOMETRIES FOR CREATING CURRENT DENSITIES IN A BIPOLAR ELECTRODE CONFIGURATION

BACKGROUND

1. Technical Field

The present disclosure relates to a forceps used for both endoscopic and open surgical procedures that includes an electrode assembly that allows a user to selectively seal and/or cut tissue. More particularly, the present disclosure relates to a forceps that uses insulators fixed between electrodes in a bipolar configuration to neck or pinch tissue to reduce the cross sectional area of the tissue.

2. Background of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing utilizes a unique combination of radiofrequency energy, clamping pressure and precise control of gap distance (i.e., distance between opposing jaw members when closed about tissue) to effectively seal or fuse tissue between two opposing jaw members or sealing plates. Vessel or tissue sealing is more than "cauterization", which involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

Tissue disposed between the jaw members of the electrosurgical forceps tends to have a relatively large tissue volume or a relatively large cross sectional area. Such a large tissue volume and/or cross sectional area leads to reduced current or energy concentrations in the zone between jaw members and electrical energy in the zone between jaw members is not easily focused.

SUMMARY

In an embodiment of the present disclosure, an end effector assembly is provided. The end effector assembly has a first jaw member having a first pair of tissue contacting surfaces and an insulator disposed therebetween. The end effector assembly also has a second jaw member that includes a second pair of tissue contacting surfaces, a pair of insulators disposed between the second pair of tissue contacting surfaces, and a cutting element disposed between the pair of insulators. The relative movement of the first jaw member toward the second jaw member causes the insulator of the first jaw member and the pair of insulators of the second jaw member to pinch tissue disposed between the first jaw member and the second jaw member.

In another embodiment of the present disclosure, an electrosurgical instrument for sealing tissue is provided. The electrosurgical instrument may include a housing, a handle assembly, and an end effector assembly. The end effector assembly has a first jaw member having a first pair of tissue contacting surfaces and an insulator disposed therebetween. The end effector assembly also has a second jaw member that includes a second pair of tissue contacting surfaces, a pair of insulators disposed between the second pair of tissue contacting surfaces, and a cutting element disposed between the pair of insulators. The relative movement of the first jaw member toward the second jaw member causes the insulator of the first jaw member and the pair of insulators of the second jaw member to pinch tissue disposed between the first jaw member and the second jaw member.

In yet another embodiment of the present disclosure another electrosurgical instrument for sealing tissue is provided. The electrosurgical instrument may include a pair of opposing shafts with each shaft having a handle at the proximal end of the shaft. The instrument may also include an end effector assembly including a pair of opposing jaw members attached at a distal end of the pair of opposing shafts wherein the opposing jaw members move from a first position to a second position by moving the pair of opposing shafts relative to one another. The pair of opposing jaw members has a first jaw member having a first pair of tissue contacting surfaces and an insulator disposed therebetween. The pair of opposing jaw members also has a second jaw member that includes a second pair of tissue contacting surfaces, a pair of insulators disposed between the second pair of tissue contacting surfaces, and a cutting element disposed between the pair of insulators. The relative movement of the first jaw member toward the second jaw member causes the insulator of the first jaw member and the pair of insulators of the second jaw member to pinch tissue disposed between the first jaw member and the second jaw member.

Energy is applied to the first pair of tissue contacting surfaces and the second pair of tissue contacting surfaces during a sealing phase. During a cutting phase, energy having a first potential is applied to the cutting element and energy having a second potential is applied to the first pair of tissue contacting surfaces and the second pair of tissue contacting surfaces. The first potential is different from the second potential.

BRIEF DESCRIPTION OF THE DRAWINGS

Objects and features of the presently disclosed systems and methods will become apparent to those of ordinary skill in the art when descriptions of various embodiments thereof are read with reference to the accompanying drawings, of which.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves. The terms "tissue" and "vessel" may be used interchangeably since it is believed that the present disclosure may be employed to seal and cut tissue or seal and cut vessels utilizing the same principles described herein.

Figure 1A:
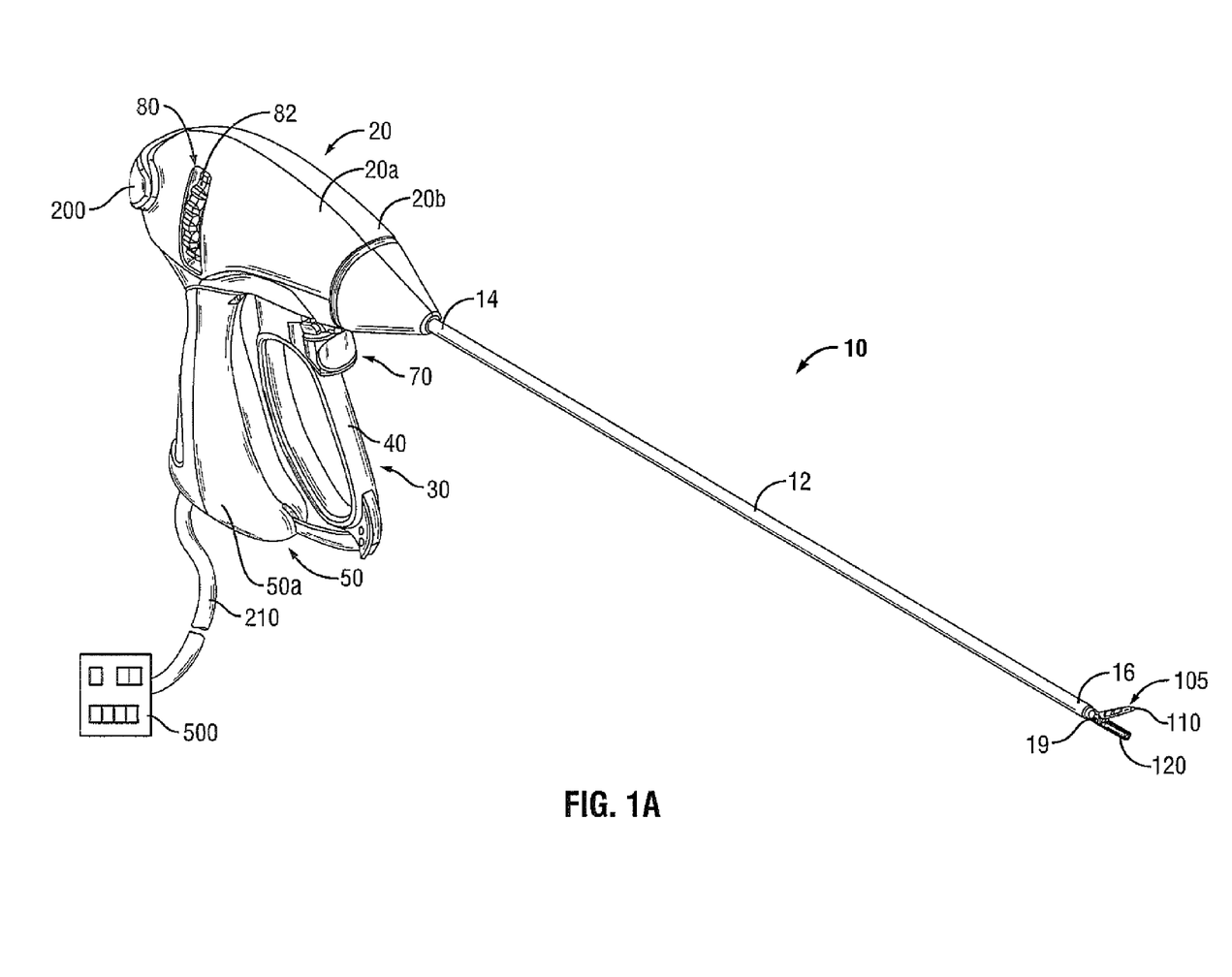
FIG. 1A is a right, perspective view of an endoscopic bipolar forceps having a housing, a shaft and a pair of jaw members affixed to a distal end thereof, the jaw members including an electrode assembly disposed therebetween.
Figure 1B:
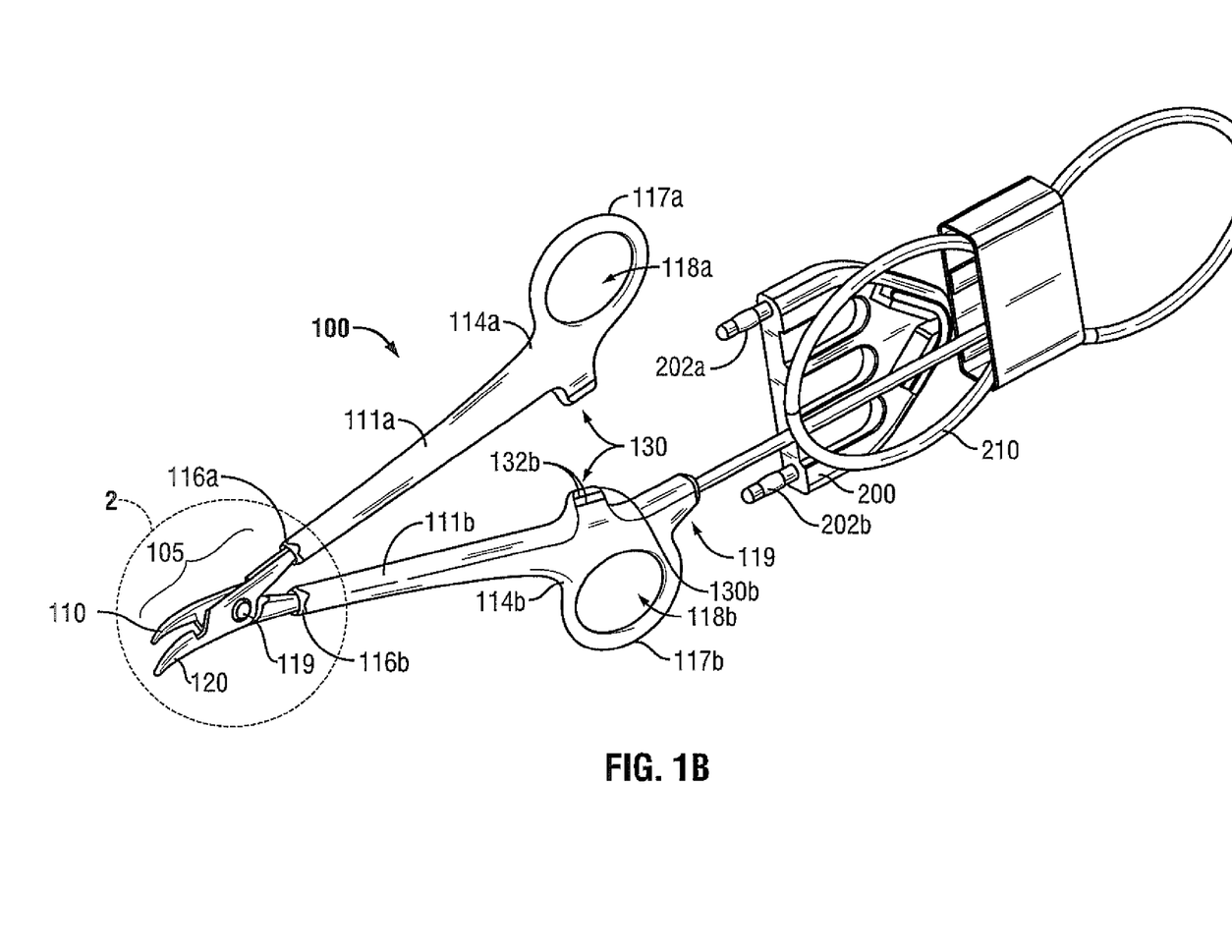
FIG. 1B is a left, perspective view of an open bipolar forceps showing a pair of first and second shafts each having a jaw member affixed to a distal end thereof with an electrode assembly disposed therebetween.

As will be described in more detail below with reference to the accompanying figures, the present disclosure is directed to the use of insulators fixed between electrodes in a bipolar configuration to "neck" or "pinch" tissue within the electrodes to reduce the cross-sectional area of tissue. By pinching the tissue, the current or energy concentration within the smaller cross-sectional area is increased. Further, the creation of a "pinch zone" or "tissue zone" allows a controllable and predictable location for energy to be concentrated, thereby leading to a predictable location for temperature to increase resulting in a controlled tissue effect. The location of the pinch geometry may be located anywhere between two bipolar electrodes Referring now to FIGS. 1A and 1B, FIG. 1A depicts a bipolar forceps 10 for use in connection with endoscopic surgical procedures and FIG. 1B depicts an open forceps 100 contemplated for use in connection with traditional open surgical procedures. For the purposes herein, either an endoscopic instrument or an open instrument may be utilized with the electrode assembly described herein. Different electrical and mechanical connections and considerations may apply to each particular type of instrument; however, the aspects with respect to the electrode assembly and its operating characteristics remain generally consistent with respect to both the open or endoscopic designs.

FIG. 1A shows a bipolar forceps 10 for use with various endoscopic surgical procedures and generally includes a housing 20, a handle assembly 30, a rotating assembly 80, a switch assembly 70 and an electrode assembly 105 having opposing jaw members 110 and 120 that mutually cooperate to grasp, seal and divide tubular vessels and vascular tissue. More particularly, forceps 10 includes a shaft 12 that has a distal end 16 dimensioned to mechanically engage the electrode assembly 105 and a proximal end 14 that mechanically engages the housing 20. The shaft 12 may include one or more known mechanically-engaging components that are designed to securely receive and engage the electrode assembly 105 such that the jaw members 110 and 120 are pivotable relative to one another to engage and grasp tissue therebetween.

The proximal end 14 of shaft 12 mechanically engages the rotating assembly 80 (not shown) to facilitate rotation of the electrode assembly 105. In the drawings and in the descriptions that follow, the term "proximal", as is traditional, will refer to the end of the forceps 10 that is closer to the user, while the term "distal" will refer to the end that is further from the user. Details relating to the mechanically cooperating components of the shaft 12 and the rotating assembly 80 are described in commonly-owned U.S. patent application Ser. No. 10/460,926, now U.S. Pat. No. 7,156,846, entitled "VESSEL SEALER AND DIVIDER FOR USE WITH SMALL TROCARS AND CANNULAS" filed on Jun. 13, 2003.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 105 as explained in more detail below. Movable handle 40 and switch assembly 70 are of unitary construction and are operatively connected to the housing 20 and the fixed handle 50 during the assembly process. Housing 20 is constructed from two component halves 20a and 20b, which are assembled about the proximal end of shaft 12 during assembly. Switch assembly is configured to selectively provide electrical energy to the electrode assembly 105.

As mentioned above, electrode assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 1B, an open forceps 100 includes a pair of elongated shaft portions 111a and 111b each having a proximal end 114a and 114b, respectively, and a distal end 116a and 116b, respectively. The forceps 100 includes jaw members 120 and 110 that attach to distal ends 116a and 116b of shafts 111a and 111b, respectively. The jaw members 110 and 120 are connected about pivot pin 119, which allows the jaw members 110 and 120 to pivot relative to one another from the first to second positions for treating tissue. The electrode assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/284,562 10/472,295, 10/116,944 and 10/179,863, now U.S. Pat. Nos. 7,582,087, 7,267,677, 7,101,372, 7,083,618 and 7,101,371 respectively.

Each shaft 111a and 111b includes a handle 117a and 117b disposed at the proximal end 114a and 114b thereof that each define a finger hole 118a and 118b, respectively, therethrough for receiving a finger of the user. As can be appreciated, finger holes 118a and 118b facilitate movement of the shafts 111a and 111b relative to one another, which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 may be included for selectively locking the jaw members 110 and 120 relative to one another at various positions during pivoting.

More particularly, the ratchet 130 includes a first mechanical interface 130a associated with shaft 111a and a second mating mechanical interface associated with shaft 111b. Each position associated with the cooperating ratchet interfaces 130a and 130b holds a specific, i.e., constant, strain energy in the shaft members 111a and 111b, which, in turn, transmits a specific closing force to the jaw members 110 and 120. The ratchet 130 may include graduations or other visual markings that enable the user to easily and quickly ascertain and control the amount of closure force desired between the jaw members 110 and 120.

As best seen in FIG. 1B, forceps 100 also includes an electrical interface or plug 200 that connects the forceps 100 to a source of electrosurgical energy, e.g., an electrosurgical generator (not explicitly shown). Plug 200 includes at least two prong members 202a and 202b that are dimensioned to mechanically and electrically connect the forceps 100 to the electrosurgical generator 500 (See FIG. 1A). An electrical cable 210 extends from the plug 200 and securely connects the cable 210 to the forceps 100. Cable 210 is internally divided within the shaft 111b to transmit electrosurgical energy through various electrical feed paths to the electrode assembly 105.

One of the shafts, e.g. 111b, includes a proximal shaft connector/flange 119 that is designed to connect the forceps 100 to a source of electrosurgical energy such as an electrosurgical generator 500. More particularly, flange 119 mechanically secures electrosurgical cable 210 to the forceps 100 such that the user may selectively apply electrosurgical energy as needed.

Figure 2:
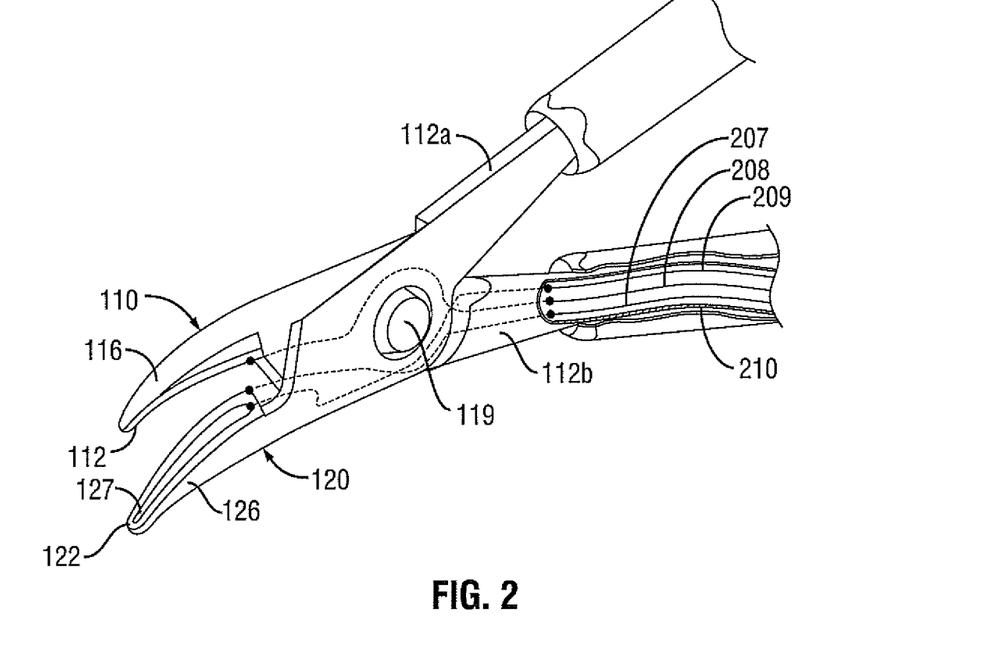
FIG. 2 is an enlarged view of the area of detail of FIG. 1B.

As best shown in the schematic illustration of FIG. 2, the jaw members 110 and 120 of both the endoscopic version of FIG. 1A and the open version of FIG. 1B are generally symmetrical and include similar component features that cooperate to permit facile rotation about pivot 19, 119 to effect the grasping and sealing of tissue. Each jaw member 110 and 120 includes an electrically conductive tissue contacting surface 112 and 122, respectively, which cooperate to engage the tissue during sealing and cutting. At least one of the jaw members, e.g., jaw member 120, includes an electrically energizable cutting element 127 disposed therein, which is explained in detail below. Together, and as shown in the various figure drawings described hereafter, the electrode assembly 105 includes the combination of the sealing electrodes 112 and 122 and the cutting element(s) 127.

The various electrical connections of the electrode assembly 105 are configured to provide electrical continuity to the tissue contacting surfaces 110 and 120 and the cutting element(s) 127 through the electrode assembly 105. For example, cable lead 210 may be configured to include three different leads, namely, leads 207, 208 and 209, which carry different electrical potentials. The cable leads 207, 208 and 209 are fed through shaft 111b and connect to various electrical connectors (not shown) disposed within the proximal end of the jaw member 110, which ultimately connect to the electrically conductive sealing surfaces 112 and 122 and cutting element(s) 127. As can be appreciated, the electrical connections may be permanently soldered to the shaft 111b during the assembly process of a disposable instrument or, alternatively, selectively removable for use with a reposable instrument.

Commonly owned U.S. patent application Ser. Nos. 10/474,170 and 10/284,562 all disclose various types of electrical connections that may be made to the jaw members 110 and 120 through the shaft 111b. In addition and with respect to the types of electrical connections which may be made to the jaw members 110 and 120 for endoscopic purposes, commonly-owned U.S. patent application Ser. Nos. 10/472,295, 10/116,944 and 10/179,863 all disclose other types of electrical connections.

The various electrical connections from lead 210 are typically dielectrically insulated from one another to allow selective and independent activation of either the tissue contacting surfaces 112 and 122 or the cutting element 127 as explained in more detail below. Alternatively, the electrode assembly 105 may include a single connector that includes an internal switch (not shown) to allow selective and independent activation of the tissue contacting surfaces 112, 122 and the cutting element 127. The leads 207, 208 and 209 (and/or conductive pathways) do not encumber the movement of the jaw members 110 and 120 relative to one another during the manipulation and grasping of tissue. Likewise, the movement of the jaw members 110 and 120 do not unnecessarily strain the lead connections.

Figure 3A:
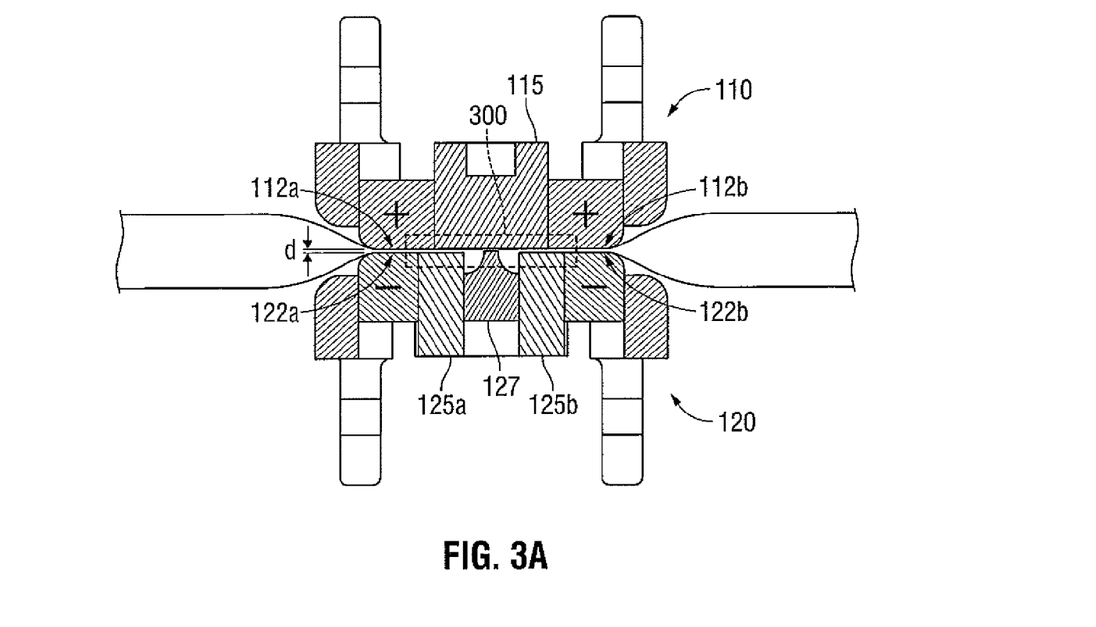
FIGS. 3A and 3B are enlarged, schematic end views showing electrode assembly configurations with tissue disposed between the jaw members according to embodiments of the present disclosure.
Figure 3B:
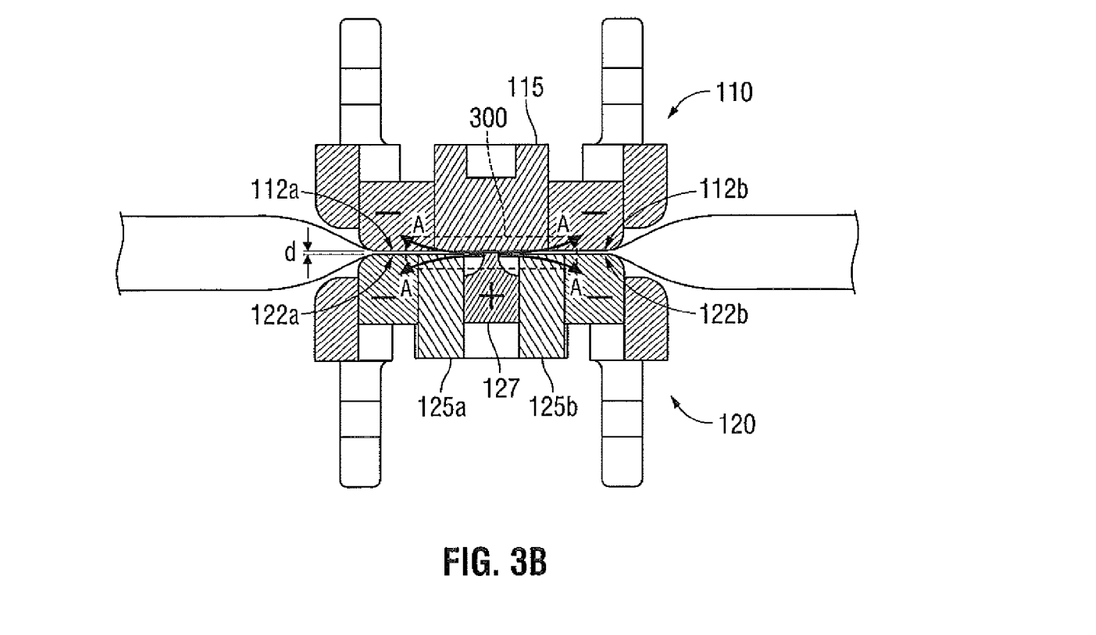

As seen in FIGS. 3A and 3B, various electrical configurations of the electrode assembly 105 are shown that are designed to effectively seal and cut tissue disposed between sealing surfaces 112a, 112b and 122a, 122b and cutting element 127 of the opposing jaw members 110 and 120, respectively. More particularly, and with respect to FIGS. 3A and 3B, jaw members 110 and 120 include conductive tissue contacting surfaces 112a, 112b and 122a, 122b, respectively, disposed along substantially the entire longitudinal length thereof (e.g., extending substantially from the proximal to distal end of the respective jaw member 110 and 120). Tissue contacting surfaces 112a, 112b and 122a, 122b may be attached to the jaw members 110, 120 by stamping, by overmolding, by casting, by overmolding a casting, by coating a casting, by overmolding a stamped electrically conductive sealing plate and/or by overmolding a metal injection molded seal plate or in other suitable ways. All of these manufacturing techniques may be employed to produce jaw member 110 and 120 having an electrically conductive tissue contacting surface 112a, 112b and 122a, 122b disposed thereon for contacting and treating tissue.

With respect to FIGS. 3A and 3B, the jaw members 110 and 120 both include an insulator or insulative material 115 and 125a, 125b, respectively, disposed between each pair of electrically conductive sealing surfaces on each jaw member 110 and 120, i.e., between pairs 112a and 112b and between pairs 122a and 122b. Insulator 115 is generally centered between tissue contacting surfaces 112a, 112b thereof along substantially the entire length of jaw member 110. Insulators 125a, 125b are generally centered along substantially the entire length of jaw member 120. Insulators 115 and 125a, 125b are arranged such that the insulator 115 generally opposes insulator 125a, 125b.

One or all of the insulators 115, 125a and 125b may be made from a ceramic material due to the hardness of the ceramic and inherent ability to withstand high temperature fluctuations. Alternatively, one or both of the insulators 113, 123 may be made from a material having a high Comparative Tracking Index (CTI) having a value in the range of about 300 to about 600 volts. Examples of high CTI materials include nylons and syndiotactic polystyrenes. Other suitable materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Jaw member 120 includes an electrically conductive cutting element 127 disposed substantially within insulators 125a, 125b. As described in detail below, the cutting element 127 may play a dual role during the sealing and cutting processes, namely: 1) to provide the necessary gap distance between conductive surfaces 112a, 112b and 122a, 122b during the sealing process; and 2) to electrically energize the tissue along the previously formed tissue seal to cut the tissue along the seal. With respect to FIGS. 3A and 313, cutting element 127 is electrically conductive; however, cutting element 127 may be made from an insulative material with a conductive coating disposed. The distance between cutting element 127 and insulator 115 may be disposed within the range of about 0.000 inches to about 0.040 inches to optimize the cutting effect.

The general characteristics of the jaw members 110 and 120 and the electrode assembly 105 will initially be described with respect to FIG. 3A while the changes to the other envisioned embodiments disclosed herein will become apparent during the description of each individual embodiment. Moreover, all of the following figures show the various electrical configurations and polarities during the "cutting phase" only. During the so called "sealing phase", the jaw members 110 and 120 are closed about tissue and the cutting element 127 may form the requisite gap between the opposing sealing surfaces 112a, 122a and 112b, 122b. During activation of the sealing phase, the cutting element 127 is not necessarily energized such that the majority of the current is concentrated between opposing sealing surfaces, 112a and 122a and 112b and 122b, to effectively seal the tissue. Stop members (not shown) may also be employed to regulate the gap distance between the sealing surfaces in lieu of or in combination with cutting element 127.

Cutting element 127 may be configured to extend beyond the tissue contacting surfaces 112a, 112b and 122a, 122b such that cutting element 127 acts as a stop member that creates a distance "d" between opposing conductive sealing surfaces 112a, 122a and 112b, 122b, which as mentioned above promotes accurate, consistent and effective tissue sealing. Distance "d" has a minimum distance of about 0.005 inches for proper effect without stopping the current flow between the cutting element 127 and tissue contacting surfaces 112a, 112b and 122a, 122b. As can be appreciated, cutting element 127 also prevents the opposing tissue contacting surfaces 112a, 122a and 112b, 122b from touching, which eliminates the chances of the forceps 10, 100 shorting during the sealing process.

Insulators 115 and 125a, 125b essentially "pinch" the tissue between the insulators 115 and 125a, 125b when tissue is grasped between jaw members 110 and 120 creating a "pinch zone" 300. Pinching of the tissue occurs when jaw members 110 and 120 are moved in to close proximity with each other. As jaw members 110 and 120 are positioned closer to each other, the surfaces of insulators 115 and 125a, 125b adjacent to the tissue squeeze or pinch the tissue walls closer to each other thereby reducing the cross-sectional area of the tissue. Alternatively, tissue may also be pinched between one of the conducting elements and the insulator. For example, tissue can be pinched between cutting element 127 and insulator 115.

During sealing, energy is applied to the tissue through the opposing sealing plates 112a, 122a and 112b, 122b to effect two tissue seals on either side of the insulators 115 and 125a, 125b. During the cutting phase, sealing electrodes 112a, 112b and 122a, 122b are energized to a first potential "−" and cutting element 127 is energized to the second electrical potential "+" such that energy flows in the direction of the indicated arrows "A". (See FIG. 3B.) In other words, it is believed that the pinching of the tissue tends to control or direct the energy concentration to specific tissue areas to effect tissue cutting.

Various geometrical configurations for the upper jaw member 110 and lower jaw member 120 may be utilized to effectively seal and subsequently cut tissue. Upper jaw member 110 and lower jaw member 120 may be disposed in a symmetrical or asymmetrical configuration. Using the various geometries of the jaw members tends to "pinch" the tissue during sealing prior to separation, which may enhance the tissue cutting process especially when the pinched tissue areas are subject to high power densities. For the purposes herein, the pinch zone may be described as the area of smallest tissue volume anywhere between the active tissue poles. Typically, the pinched tissue area is associated with high pressure. Moreover, any combination of electrical potential as hereinbefore described may be utilized with the various jaw members 110 and 120 (and each jaw member's opposing jaw member) to effectively seal tissue during a first electrical phase and cut tissue during a subsequent electrical phase. As such, the illustrated jaw members 110 and 120 are labeled with a first electrical potential "−" and a second electrical potential "+"; however, the lower jaw member 120 inclusive of the sealing surfaces 122a and 122b and cutting element 127 (which may or may not be a mirror image of the upper jaw member) may be energized with any combination of first and second electrical potential(s) (or other electrical potentials) to effectively seal and subsequently cut tissue disposed between the jaw members 110 and 120.

Conductive cutting element 127 is oriented in opposing, vertical registration within insulators 125a and 125b jaw member 120. Cutting element 127 may be substantially dull so as to not inhibit the sealing process (e.g., premature cutting) during the sealing phase of the electrosurgical activation. In other words, the surgeon is free to manipulate, grasp and clamp the tissue for sealing purposes without cutting element 127 mechanically cutting into the tissue. Moreover, in this instance, tissue cutting can be achieved through a combination of mechanically clamping the tissue between cutting element 127 and applying electrosurgical energy from cutting element 127 (by activating, through the tissue and to the return electrodes, i.e., the electrically conductive tissue contacting surfaces 112a, 112b and 122a, 122b) as shown in FIG. 3B.

The geometrical configuration of cutting element 127 may play an important role in determining the overall effectiveness of the tissue cut. For example, the power density and/or current concentration around cutting element 127 is based upon the particular geometrical configuration of the cutting element 127 and the cutting element's 127 proximity to the return electrodes, i.e., tissue contacting surfaces 112a, 112b and 122a, 122b. Certain geometries of the cutting element 127 may create higher areas of power density than other geometries. Moreover, the spacing of the return electrodes 112a, 112b and 122a, 122b to these current concentrations affects the electrical fields through the tissue. Therefore, by configuring cutting element 127 and the respective insulators 115 and 125a, 125b within close proximity to one another, the electrical power density remains high, which is ideal for cutting and the instrument will not short due to accidental contact between conductive surfaces. The relative size of cutting element 127 and/or the size of the insulator 115 and 125a, 125b may be selectively altered depending upon a particular or desired purpose to produce a particular surgical effect.

In addition, the cutting element 127 may be independently activated by the surgeon or automatically activated by the generator once sealing is complete. A safety algorithm may be employed to assure that an accurate and complete tissue seal is formed before cutting. An audible or visual indicator (not shown) may be employed to assure the surgeon that an accurate seal has been formed and the surgeon may be required to activate a trigger (or deactivate a safety) before cutting. For example, a smart sensor or feedback algorithm may be employed to determine seal quality prior to cutting. The smart sensor or feedback loop may also be configured to automatically switch electrosurgical energy to the cutting element 127 once the smart sensor determines that the tissue is properly sealed. The electrical configuration of the electrically conductive sealing surfaces 112a, 112b and 122a, 122b may also be automatically or manually altered during the sealing and cutting processes to effect accurate and consistent tissue sealing and cutting.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An end effector assembly, comprising:
   a first jaw member having a first pair of electrically-conductive tissue contacting surfaces and an insulator disposed therebetween;
   a second jaw member including:
      a second pair of electrically-conductive tissue contacting surfaces;
      a pair of insulators disposed between the second pair of electrically-conductive tissue contacting surfaces; and
      an electrically energizable cutting element fixedly disposed relative to and between the pair of insulators;
   wherein relative movement of the first jaw member toward the second jaw member causes the insulator of the first jaw member and the pair of insulators of the second jaw member to pinch tissue adjacent both sides of the electrically energizable cutting element.

2. The end effector assembly of claim 1, wherein energy is applied to the first pair of electrically-conductive tissue contacting surfaces and the second pair of electrically-conductive tissue contacting surfaces during a sealing phase.

3. The end effector assembly of claim 1, wherein energy having a first potential is applied to the electrically energizable cutting element and energy having a second potential is applied to the first pair of electrically-conductive tissue contacting surfaces and the second pair of electrically-conductive tissue contacting surfaces during a cutting phase.

4. The end effector assembly of claim 3, wherein the first potential is different from the second potential.

5. The end effector assembly of claim 1, wherein the electrically energizable cutting element is configured to provide a gap distance between the first pair of electrically conductive tissue contacting surfaces and the second pair of electrically conductive tissue contacting surfaces.

6. An electrosurgical instrument, comprising:
   a housing;
   a handle assembly; and
   an end effector assembly including:
      a first jaw member having a first pair of electrically-conductive tissue contacting surfaces and an insulator disposed therebetween;
      a second jaw member including:
         a second pair of electrically-conductive tissue contacting surfaces;
         a pair of insulators disposed between the second pair of electrically-conductive tissue contacting surfaces; and
         an electrically energizable cutting element fixedly disposed relative to and between the pair of insulators;
      wherein relative movement of the first jaw member toward the second jaw member causes the insulator of the first jaw member and the pair of insulators of the second jaw member to pinch tissue adjacent both sides of the electrically energizable cutting element.

7. The electrosurgical instrument of claim 6, wherein energy is applied to the first pair of electrically-conductive tissue contacting surfaces and the second pair of electrically-conductive tissue contacting surfaces during a sealing phase.

8. The electrosurgical instrument of claim 6, wherein energy having a first potential is applied to the electrically energizable cutting element and energy having a second potential is applied to the first pair of electrically-conductive tissue contacting surfaces and the second pair of electrically-conductive tissue contacting surfaces during a cutting phase.

9. The electrosurgical instrument of claim 8, wherein the first potential is different from the second potential.

10. An electrosurgical instrument for sealing tissue, comprising:
    a pair of opposing shafts, each shaft having a handle at the proximal end of the shaft; and
    an end effector assembly including a pair of opposing jaw members attached at a distal end of the pair of opposing shafts wherein the opposing jaw members move from a first position to a second position by moving the pair of opposing shafts relative to one another, the pair of opposing jaw members including:
       a first jaw member having a first pair of electrically-conductive tissue contacting surfaces and an insulator disposed therebetween;
       a second jaw member including:
          a second pair of electrically-conductive tissue contacting surfaces;
          a pair of insulators disposed between the second pair of electrically-conductive tissue contacting surfaces; and
          an electrically energizable cutting element fixedly disposed relative to and between the pair of insulators;
       wherein relative movement of the first jaw member toward the second jaw member causes the insulator of the first jaw member and the pair of insulators of the second jaw member to pinch tissue adjacent both sides of the electrically energizable cutting element.

11. The electrosurgical instrument of claim 10, wherein energy is applied to the first pair of electrically-conductive tissue contacting surfaces and the second pair of electrically-conductive tissue contacting surfaces during a sealing phase.

12. The electrosurgical instrument of claim 10, wherein energy having a first potential is applied to the electrically energizable cutting element and energy having a second potential is applied to the first pair of electrically-conductive tissue contacting surfaces and the second pair of electrically-conductive tissue contacting surfaces during a cutting phase.

13. The electrosurgical instrument of claim 12, wherein the first potential is different from the second potential.

* * * * *